United States Patent
Thomas et al.

(10) Patent No.: US 12,429,877 B2
(45) Date of Patent: Sep. 30, 2025

(54) SELF-PROTECTION OF ROBOTIC VEHICLES IN INVISIBLE HAZARDOUS GASEOUS SURROUNDING

(71) Applicant: International Business Machines Corporation, Armonk, NY (US)

(72) Inventors: Binoy Thomas, Kozhikode (IN); Sudheesh S. Kairali, Kozhikode (IN); Sarbajit K. Rakshit, Kolkata (IN)

(73) Assignee: International Business Machines Corporation, Armonk, NY (US)

( * ) Notice: Subject to any disclaimer, the term of this patent is extended or adjusted under 35 U.S.C. 154(b) by 203 days.

(21) Appl. No.: 18/351,536

(22) Filed: Jul. 13, 2023

(65) Prior Publication Data

US 2025/0021095 A1    Jan. 16, 2025

(51) Int. Cl.
*G05D 1/00*  (2024.01)
*G01N 33/00*  (2006.01)

(52) U.S. Cl.
CPC ....... *G05D 1/0214* (2013.01); *G01N 33/0063* (2013.01); *G05D 1/0219* (2013.01)

(58) Field of Classification Search
None
See application file for complete search history.

(56) References Cited

U.S. PATENT DOCUMENTS

| | | | |
|---|---|---|---|
| 5,107,768 A * | 4/1992 | Langenohl | F42B 30/08 102/293 |
| 8,355,818 B2 | 1/2013 | Nielsen | |
| 10,757,536 B2 * | 8/2020 | Jurzak | H04W 4/023 |
| 2020/0234601 A1 * | 7/2020 | Ivanov | G09B 29/007 |

(Continued)

FOREIGN PATENT DOCUMENTS

| | | |
|---|---|---|
| CN | 104870147 A | 9/2016 |
| CN | 107878584 B | 4/2018 |

(Continued)

OTHER PUBLICATIONS

Dol, Sharul Sham, et al., "An Improved Smoke-Wire Flow Visualization Technique", Aug. 23, 2006, WSEAS International Conference of Fluid Mechanics and Aerodynamics (Year: 2006).*

(Continued)

*Primary Examiner* — Navid Z. Mehdizadeh
*Assistant Examiner* — Sarah A. Mueller
(74) *Attorney, Agent, or Firm* — Elliot J. Shine (57) ABSTRACT

A computer-implemented system and method protect a robot in a hazardous environment. The method comprises detecting, with a hazardous environment detector, the presence of a hazardous gas within a bounded environment defining the boundaries of the hazardous environment, and detecting a wind flow speed and wind flow direction proximate the hazardous environment detector. The method further comprises determining a hazardous gas concentration (HGC) that is at least one of a present HGC and a predicted future HGC, and reading, from a database, a maximum HGC for at least one of the robot and a payload of the robot. Conditioned upon the HGC exceeding a threshold value of the maximum HGC, the method directs the robot to move to a safe location in which the HGC does not exceed the threshold value of the maximum HGC.

19 Claims, 4 Drawing Sheets

(56) References Cited

U.S. PATENT DOCUMENTS

| | | |
|---|---|---|
| 2021/0124356 A1 | 4/2021 | Wolfe |
| 2023/0051111 A1 | 2/2023 | Cyrus |

FOREIGN PATENT DOCUMENTS

| | | | | |
|---|---|---|---|---|
| CN | 110834326 A | | 2/2020 | |
| CN | 112270112 A | * | 1/2021 | |
| CN | 113804653 A | * | 12/2021 | ............ G01N 21/25 |
| CN | 108006439 B | | 11/2022 | |
| KR | 20170014146 A | * | 2/2017 | |

OTHER PUBLICATIONS

Joshna, V., et al., "Fully Autonomous Robot to Detect and Degasify Hazardous Gas after Flood Disaster", Aug. 23, 2019, IEEE (Year: 2019).*

Machine translation of specification of Kim (KR-20170014146-A), 2017 (Year: 2017).*

Machine translation of claims of Lou et al. (CN-112270112-A), 2021 (Year: 2021).*

Machine translation of Chen et al. (CN-113804653-A) (Year: 2021).*

"Metals and mining industry digital solutions optimize operations", IBM, 8 pages, downloaded from the Internet on May 23, 2023, <https://www.ibm.com/industries/metals-mining>.

"What is robotic process automation (RPA)?", IBM, downloaded from the Internet on May 23, 2023, 11 pages, <https://www.ibm.com/topics/rpa>.

Murphy, Patrick, "The Manufacturing Side of Digital Transformation: Smart Factories", IBM Think Blog, Mar. 4, 2019, 7 pages, <https://www.ibm.com/blogs/think/2019/03/the-manufacturing-side-of-digital-transformation-smart-factories/>.

Trevelyan et al., "Robotics in Hazardous Applications", Jan. 2008, In book: Springer Handbook of Robotics, pp. 1101-1126, DOI:10.1007/978-3-540-30301-5_49.

* cited by examiner

SELF-PROTECTION OF ROBOTIC VEHICLES IN INVISIBLE HAZARDOUS GASEOUS SURROUNDING

BACKGROUND

A system and method are described below for the protection of robotic systems and vehicles in invisible hazardous situations.

Robotic systems are used for performing various activities, such as material movement in an industrial facility, investigating the surroundings of an area, etc. While robotic systems are performing their activities, different types of hazardous situations may be present. These hazardous situations might cause damage to the robotic systems and/or robotic vehicles (hereinafter "robots") within the robotic systems. Examples of hazardous situations may include the presence of flammable gas, poisonous gas, oil leaks, or other chemical leaks, etc., and the hazards presented in such situations may not be visible.

SUMMARY

Disclosed herein is a computer-implemented method for protecting a robot in a hazardous environment. The method comprises detecting, with a hazardous environment detector, the presence of a hazardous gas within a bounded environment defining the boundaries of the hazardous environment, and detecting a wind flow speed and wind flow direction proximate the hazardous environment detector. The method further comprises determining a hazardous gas concentration (HGC) that is at least one of a present HGC and a predicted future HGC, and reading, from a database, a maximum HGC for at least one of the robot and a payload of the robot. Conditioned upon the HGC exceeding a threshold value of the maximum HGC, the method directs the robot to move to a safe location in which the HGC does not exceed the threshold value of the maximum HGC.

Disclosed herein is also a system for protecting a robot in a hazardous environment. The system comprises a memory, and a processor. The processor is configured to detect, with a hazardous environment detector, the presence of a hazardous gas within a bounded environment defining the boundaries of the hazardous environment. The processor is also configured to detect a wind flow speed and wind flow direction proximate the hazardous environment detector, determine a hazardous gas concentration (HGC) that is at least one of a present HGC and a predicted future HGC. The processor is configured to read, from a database, a maximum HGC for at least one of the robot and a payload of the robot, and conditioned upon the HGC exceeding a threshold value of the maximum HGC, direct the robot to move to a safe location in which the HGC does not exceed the threshold value of the maximum HGC.

Furthermore, embodiments may take the form of a related computer program product, accessible from a computer-usable or computer-readable medium providing program code for use, by, or in connection, with a computer or any instruction execution system. For the purpose of this description, a computer-usable or computer-readable medium may be any apparatus that may contain a mechanism for storing, communicating, propagating or transporting the program for use, by, or in connection, with the instruction execution system, apparatus, or device.

BRIEF DESCRIPTION OF THE DRAWINGS

Various embodiments are described herein with reference to different subject-matter. In particular, some embodiments may be described with reference to methods, whereas other embodiments may be described with reference to apparatuses and systems. However, a person skilled in the art will gather from the above and the following description that, unless otherwise notified, in addition to any combination of features belonging to one type of subject-matter, also any combination between features relating to different subject-matter, in particular, between features of the methods, and features of the apparatuses and systems, are considered as to be disclosed within this document.

The aspects defined above, and further aspects disclosed herein, are apparent from the examples of one or more embodiments to be described hereinafter and are explained with reference to the examples of the one or more embodiments, but to which the invention is not limited. Various embodiments are described, by way of example only, and with reference to the following drawings.

DETAILED DESCRIPTION

The following general acronyms may be used below:
CD-ROM compact disc ROM
CPP computer program product
DVD digital versatile disk
EPROM erasable programmable read-only memory
EUD end-user device
IoT Internet of Things
LAN local-area network
NFC near field communication
RAM random access memory
ROM read-only memory
SAN storage area network
SD secure digital
SDN software-defined networking
SRAM static random-access memory
UI user interface
USB universal serial bus
VCE virtual computing environment
WAN wide-area network Table 1

General Acronyms

Data Processing System in General

Various aspects of the present disclosure are described by narrative text, flowcharts, block diagrams of computer systems and/or block diagrams of the machine logic included in computer program product (CPP) embodiments. With respect to any flowcharts, depending upon the technology involved, the operations can be performed in a different order than what is shown in a given flowchart. For example, again depending upon the technology involved, two operations shown in successive flowchart blocks may be performed in reverse order, as a single integrated step, concurrently, or in a manner at least partially overlapping in time.

A computer program product embodiment ("CPP embodiment" or "CPP") is a term used in the present disclosure to describe any set of one, or more, storage media (also called "mediums") collectively included in a set of one, or more, storage devices that collectively include machine readable code corresponding to instructions and/or data for performing computer operations specified in a given CPP claim. A "storage device" is any tangible device that can retain and store instructions for use by a computer processor. Without limitation, the computer readable storage medium may be an electronic storage medium, a magnetic storage medium, an optical storage medium, an electromagnetic storage medium, a semiconductor storage medium, a mechanical storage medium, or any suitable combination of the foregoing. Some known types of storage devices that include these mediums include: diskette, hard disk, random access memory (RAM), read-only memory (ROM), erasable programmable read-only memory (EPROM or Flash memory), static random access memory (SRAM), compact disc read-only memory (CD-ROM), digital versatile disk (DVD), memory stick, floppy disk, mechanically encoded device (such as punch cards or pits/lands formed in a major surface of a disc) or any suitable combination of the foregoing. A computer readable storage medium, as that term is used in the present disclosure, is not to be construed as storage in the form of transitory signals per se, such as radio waves or other freely propagating electromagnetic waves, electromagnetic waves propagating through a waveguide, light pulses passing through a fiber optic cable, electrical signals communicated through a wire, and/or other transmission media. As will be understood by those of skill in the art, data is typically moved at some occasional points in time during normal operations of a storage device, such as during access, de-fragmentation or garbage collection, but this does not render the storage device as transitory because the data is not transitory while it is stored.

Figure 1:
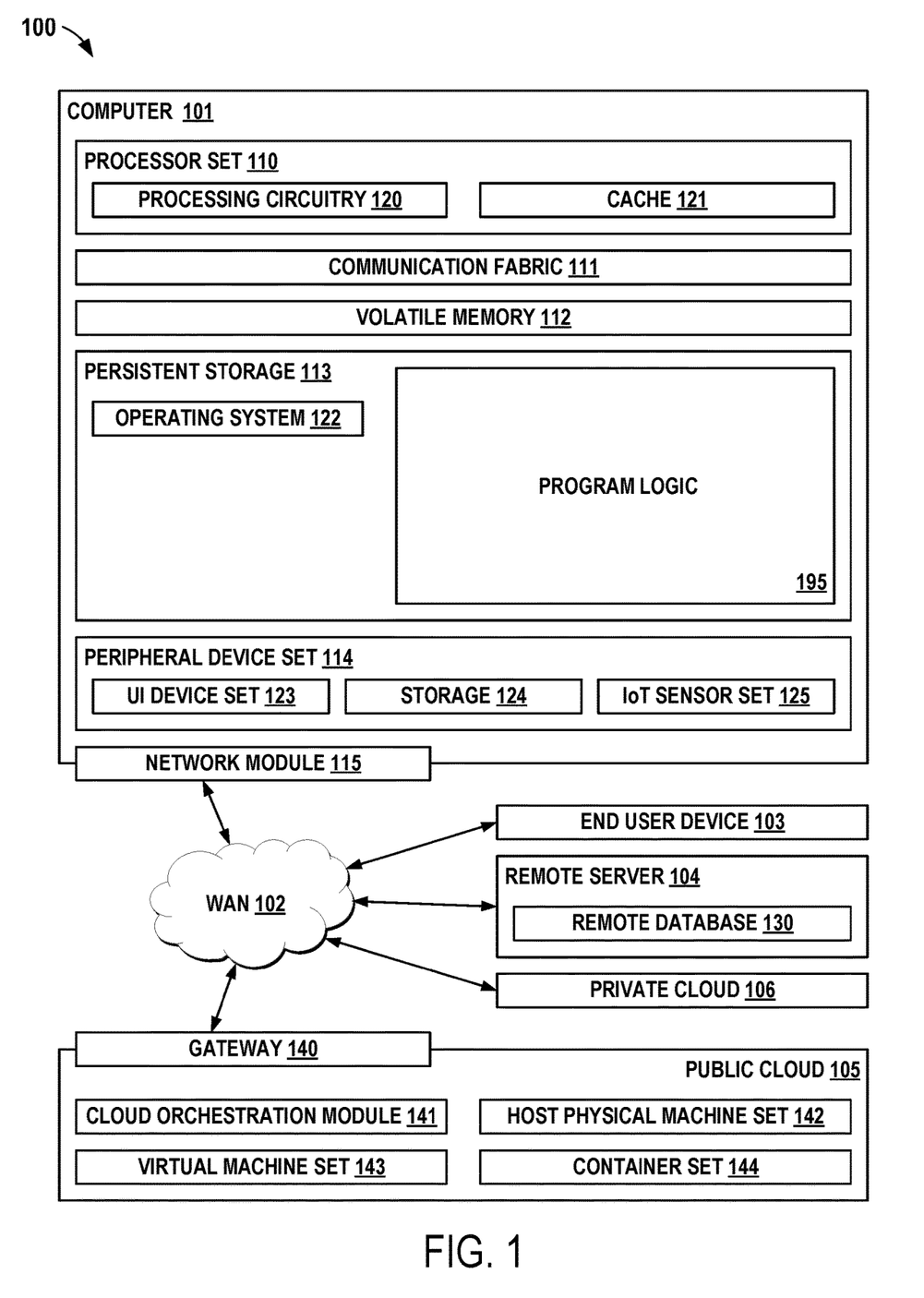
FIG. 1 is a block diagram of a general computing device and environment.

FIG. 1 is a block diagram of a general computing device and environment. Computing environment 100 contains an example of an environment for the execution of at least some of the computer code involved in performing the inventive methods disclosed herein, including program logic 195 that may be implemented in various combinations of hardware and/or software described below. In addition to the program logic 195, computing environment 100 includes, for example, computer 101, wide area network (WAN) 102, end user device (EUD) 103, remote server 104, public cloud 105, and private cloud 106. In this embodiment, computer 101 includes processor set 110 (including processing circuitry 120 and cache 121), communication fabric 111, volatile memory 112, persistent storage 113 (including operating system 122 and program logic 195, as identified above), peripheral device set 114 (including user interface (UI) device set 123, storage 124, and Internet of Things (IoT) sensor set 125), and network module 115. Remote server 104 includes remote database 130. Public cloud 105 includes gateway 140, cloud orchestration module 141, host physical machine set 142, virtual machine set 143, and container set 144.

COMPUTER 101 may take the form of a desktop computer, laptop computer, tablet computer, smart phone, smart watch or other wearable computer, mainframe computer, quantum computer or any other form of computer or mobile device now known or to be developed in the future that is capable of running a program, accessing a network or querying a database, such as remote database 130. As is well understood in the art of computer technology, and depending upon the technology, performance of a computer-implemented method may be distributed among multiple computers and/or between multiple locations. On the other hand, in this presentation of computing environment 100, detailed discussion is focused on a single computer, specifically computer 101, to keep the presentation as simple as possible. Computer 101 may be located in a cloud, even though it is not shown in a cloud in FIG. 1. On the other hand, computer 101 is not required to be in a cloud except to any extent as may be affirmatively indicated.

PROCESSOR SET 110 includes one, or more, computer processors of any type now known or to be developed in the future. Processing circuitry 120 may be distributed over multiple packages, for example, multiple, coordinated integrated circuit chips. Processing circuitry 120 may implement multiple processor threads and/or multiple processor cores. Cache 121 is memory that is located in the processor chip package(s) and is typically used for data or code that should be available for rapid access by the threads or cores running on processor set 110. Cache memories are typically organized into multiple levels depending upon relative proximity to the processing circuitry. Alternatively, some, or all, of the cache for the processor set may be located "off chip." In some computing environments, processor set 110 may be designed for working with qubits and performing quantum computing.

Computer readable program instructions are typically loaded onto computer 101 to cause a series of operational steps to be performed by processor set 110 of computer 101 and thereby effect a computer-implemented method, such that the instructions thus executed will instantiate the methods specified in flowcharts and/or narrative descriptions of computer-implemented methods included in this document (collectively referred to as "the inventive methods"). These computer readable program instructions are stored in various types of computer readable storage media, such as cache 121 and the other storage media discussed below. The program instructions, and associated data, are accessed by processor set 110 to control and direct performance of the inventive methods. In computing environment 100, at least some of the instructions for performing the inventive methods may be stored in the program logic 195 in persistent storage 113.

COMMUNICATION FABRIC 111 is the signal conduction path that allows the various components of computer 101 to communicate with each other. Typically, this fabric is made of switches and electrically conductive paths, such as the switches and electrically conductive paths that make up busses, bridges, physical input/output ports and the like. Other types of signal communication paths may be used, such as fiber optic communication paths and/or wireless communication paths.

VOLATILE MEMORY 112 is any type of volatile memory now known or to be developed in the future. Examples include dynamic type random access memory (RAM) or static type RAM. Typically, volatile memory 112 is characterized by random access, but this is not required unless affirmatively indicated. In computer 101, the volatile memory 112 is located in a single package and is internal to computer 101, but, alternatively or additionally, the volatile memory may be distributed over multiple packages and/or located externally with respect to computer 101.

PERSISTENT STORAGE 113 is any form of non-volatile storage for computers that is now known or to be developed in the future. The non-volatility of this storage means that the stored data is maintained regardless of whether power is being supplied to computer 101 and/or directly to persistent storage 113. Persistent storage 113 may be a read only memory (ROM), but typically at least a portion of the persistent storage allows writing of data, deletion of data and re-writing of data. Some familiar forms of persistent storage include magnetic disks and solid state storage devices. Operating system 122 may take several forms, such as various known proprietary operating systems or open source Portable Operating System Interface-type operating systems that employ a kernel. The code included in the program logic 195 typically includes at least some of the computer code involved in performing the inventive methods.

PERIPHERAL DEVICE SET 114 includes the set of peripheral devices of computer 101. Data communication connections between the peripheral devices and the other components of computer 101 may be implemented in various ways, such as Bluetooth connections, Near-Field Communication (NFC) connections, connections made by cables (such as universal serial bus (USB) type cables), insertion-type connections (for example, secure digital (SD) card), connections made through local area communication networks and even connections made through wide area networks such as the internet. In various embodiments, UI device set 123 may include components such as a display screen, speaker, microphone, wearable devices (such as goggles and smart watches), keyboard, mouse, printer, touchpad, game controllers, and haptic devices. Storage 124 is external storage, such as an external hard drive, or insertable storage, such as an SD card. Storage 124 may be persistent and/or volatile. In some embodiments, storage 124 may take the form of a quantum computing storage device for storing data in the form of qubits. In embodiments where computer 101 is required to have a large amount of storage (for example, where computer 101 locally stores and manages a large database) then this storage may be provided by peripheral storage devices designed for storing very large amounts of data, such as a storage area network (SAN) that is shared by multiple, geographically distributed computers. IoT sensor set 125 is made up of sensors that can be used in Internet of Things applications. For example, one sensor may be a thermometer and another sensor may be a motion detector.

NETWORK MODULE 115 is the collection of computer software, hardware, and firmware that allows computer 101 to communicate with other computers through WAN 102. Network module 115 may include hardware, such as modems or Wi-Fi signal transceivers, software for packetizing and/or de-packetizing data for communication network transmission, and/or web browser software for communicating data over the internet. In some embodiments, network control functions and network forwarding functions of network module 115 are performed on the same physical hardware device. In other embodiments (for example, embodiments that utilize software-defined networking (SDN)), the control functions and the forwarding functions of network module 115 are performed on physically separate devices, such that the control functions manage several different network hardware devices. Computer readable program instructions for performing the inventive methods can typically be downloaded to computer 101 from an external computer or external storage device through a network adapter card or network interface included in network module 115.

WAN 102 is any wide area network (for example, the internet) capable of communicating computer data over non-local distances by any technology for communicating computer data, now known or to be developed in the future. In some embodiments, the WAN 102 may be replaced and/or supplemented by local area networks (LANs) designed to communicate data between devices located in a local area, such as a Wi-Fi network. The WAN and/or LANs typically include computer hardware such as copper transmission cables, optical transmission fibers, wireless transmission, routers, firewalls, switches, gateway computers and edge servers.

END USER DEVICE (EUD) 103 is any computer system that is used and controlled by an end user (for example, a customer of an enterprise that operates computer 101), and may take any of the forms discussed above in connection with computer 101. EUD 103 typically receives helpful and useful data from the operations of computer 101. For example, in a hypothetical case where computer 101 is designed to provide a recommendation to an end user, this recommendation would typically be communicated from network module 115 of computer 101 through WAN 102 to EUD 103. In this way, EUD 103 can display, or otherwise present, the recommendation to an end user. In some embodiments, EUD 103 may be a client device, such as thin client, heavy client, mainframe computer, desktop computer and so on.

REMOTE SERVER 104 is any computer system that serves at least some data and/or functionality to computer 101. Remote server 104 may be controlled and used by the same entity that operates computer 101. Remote server 104 represents the machine(s) that collect and store helpful and useful data for use by other computers, such as computer 101. For example, in a hypothetical case where computer 101 is designed and programmed to provide a recommendation based on historical data, then this historical data may be provided to computer 101 from remote database 130 of remote server 104.

PUBLIC CLOUD 105 is any computer system available for use by multiple entities that provides on-demand availability of computer system resources and/or other computer capabilities, especially data storage (cloud storage) and computing power, without direct active management by the user. Cloud computing typically leverages sharing of resources to achieve coherence and economics of scale. The direct and active management of the computing resources of public cloud 105 is performed by the computer hardware and/or software of cloud orchestration module 141. The computing resources provided by public cloud 105 are typically implemented by virtual computing environments that run on various computers making up the computers of host physical machine set 142, which is the universe of physical computers in and/or available to public cloud 105. The virtual computing environments (VCEs) typically take the form of virtual machines from virtual machine set 143 and/or containers from container set 144. It is understood that these VCEs may be stored as images and may be transferred among and between the various physical machine hosts, either as images or after instantiation of the VCE. Cloud orchestration module 141 manages the transfer and storage of images, deploys new instantiations of VCEs and manages active instantiations of VCE deployments. Gateway 140 is the collection of computer software, hardware, and firmware that allows public cloud 105 to communicate through WAN 102.

Some further explanation of virtualized computing environments (VCEs) will now be provided. VCEs can be stored as "images." A new active instance of the VCE can be instantiated from the image. Two familiar types of VCEs are virtual machines and containers. A container is a VCE that uses operating-system-level virtualization. This refers to an operating system feature in which the kernel allows the existence of multiple isolated user-space instances, called containers. These isolated user-space instances typically behave as real computers from the point of view of programs running in them. A computer program running on an ordinary operating system can utilize all resources of that computer, such as connected devices, files and folders, network shares, CPU power, and quantifiable hardware capabilities. However, programs running inside a container can only use the contents of the container and devices assigned to the container, a feature which is known as containerization.

PRIVATE CLOUD 106 is similar to public cloud 105, except that the computing resources are only available for use by a single enterprise. While private cloud 106 is depicted as being in communication with WAN 102, in other embodiments a private cloud may be disconnected from the internet entirely and only accessible through a local/private network. A hybrid cloud is a composition of multiple clouds of different types (for example, private, community or public cloud types), often respectively implemented by different vendors. Each of the multiple clouds remains a separate and discrete entity, but the larger hybrid cloud architecture is bound together by standardized or proprietary technology that enables orchestration, management, and/or data/application portability between the multiple constituent clouds. In this embodiment, public cloud 105 and private cloud 106 are both part of a larger hybrid cloud.

The descriptions of the various embodiments of the present invention are presented for purposes of illustration, but are not intended to be exhaustive or limited to the embodiments disclosed. Many modifications and variations will be apparent to those of ordinary skill in the art without departing from the scope and spirit of the described embodiments. The terminology used herein has been chosen to best explain the principles of the embodiments, the practical application or technical improvement over technologies found in the marketplace, or to enable others of ordinary skill in the art to understand the embodiments disclosed herein.

Certain reference numbers or characters may be represented as being pluralities (e.g., 100.1, 100.2, or 100A, 100B, etc.). In such instances, reference to a single reference number (e.g., 100) may represent the plurality of entities, or may represent an example of the set, depending on the context. This similarly applies to reference numbers or characters that use subscripts.

Self-Protection of Robotic Vehicles in Invisible Hazardous Gaseous Surrounding

In certain situations, robots that perform activities within a robotic system may encounter a hazardous surrounding, such as an environment filled with flammable or poisonous gas. Some robots are able to handle these hazardous situations and others are not. Robots for handling hazardous situations typically require greater resources in terms of additional protective materials and the like. Thus, from a cost perspective, it may be prudent to utilize unprotected robots in various situations initially, and only if a hazardous situation or environment is detected are better-protected robots be sent in.

While robots within a particular robotic system are performing activities in any surrounding, if the surrounding becomes hazardous, then the unprotected robots may leave the hazardous environment to avoid damage. In their place, protected robots are assigned to continue the activity and/or address the hazardous environment. Thus, when the unprotected robots find themselves in a hazardous surrounding, they remove themselves from the hazardous surrounding or at least an appropriate mobility path is identified to allow the unprotected robots to leave.

Figure 2:
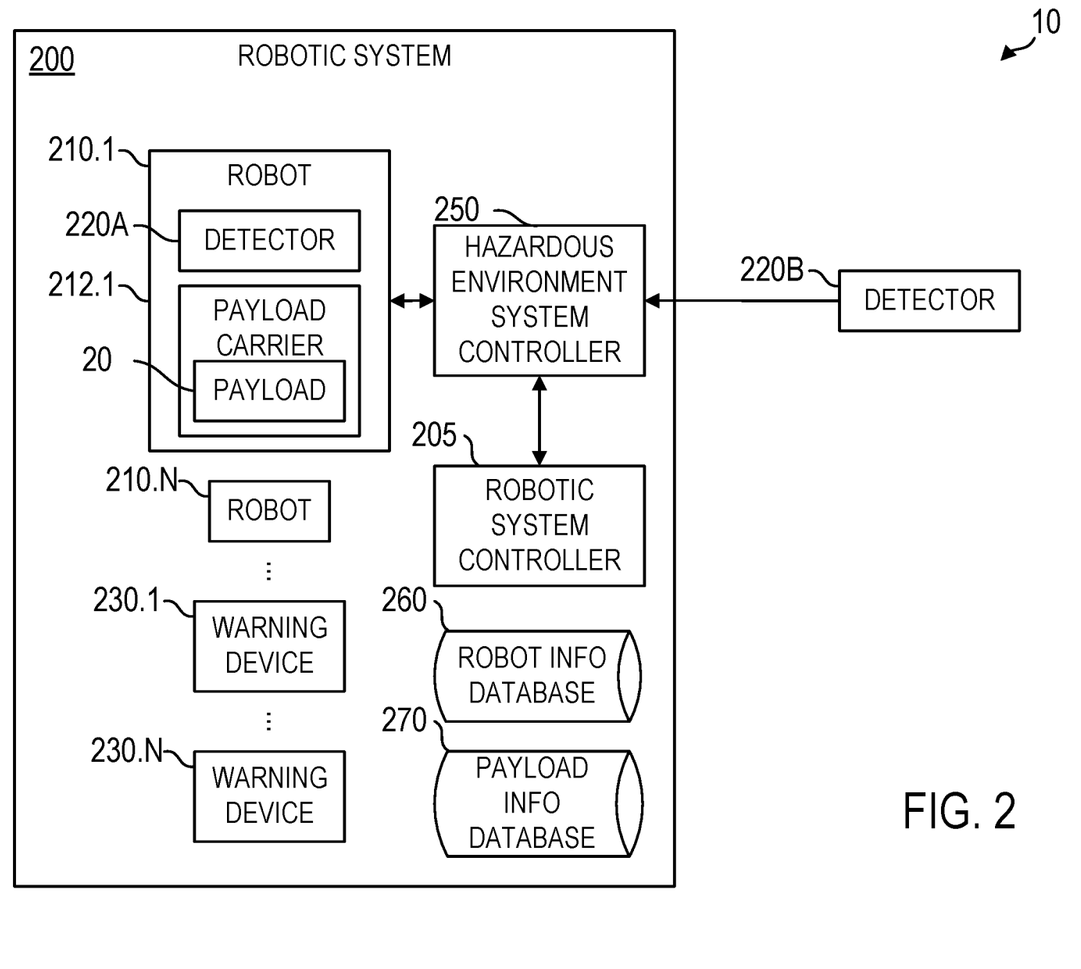
FIG. 2 is a block diagram illustrating an example environment in which the use of a robotic system and a hazardous environment system controller may operate, according to some embodiments.

FIG. 2 is a block diagram illustrating an example robotic system 200 that may operate within, for example, an environment 10. The environment may utilize some or all of the components of the computer environment 100. The robotic system 200 contains a robotic system controller 205 that may be implemented using, e.g., a computer 101. The robotic system 200 may further comprise a hazardous environment system 250 that may also be implemented using, e.g., the computer 101 and may perform various functions described herein, and may, for example, be implemented in the program logic 195. The robotic system controller 205 and a hazardous environment system controller (HESC) 250 may be able to communicate with one another via a network interface or computer bus, as described above.

The robotic system 200 may contain one or more robots 210.1-210N (210). In addition to mobility hardware and software (not shown) that permits motion of the robot 210, each robot 210 may comprise a payload carrier 212.1 that is capable of carrying a payload 20. The payload carrier 212.1 may be unsealed or open to the environment, meaning the payload 20 may be exposed to the hazardous environment. Alternately, the payload carrier 212.1 may be scaled and provide some protection against various hazardous environments for the payload 20.

The robotic system 200 may comprise a robot information database 260 that comprises information about the robots 210 in the robotic system 200—both those robots 210 currently in operation and those robots 210 that may be made available for operation. The robot information may comprise basic mechanical information about each robot 210, such as size parameters, weight, travel speed, operating speed, its payload carrier 212 (e.g., size of payload carrier 212, protecting/non-protecting status and/or degree of protection for various hazardous gasses and/or respective concentrations of those gasses), etc. The robot system controller 205 and the HESC 250 may access the robot information database 260 to determine the operational status of the robotic system 200 and determined hazardous situation for the environment 10 at any particular time.

The robotic system 200 may also comprise a payload information database 270 that provides information about various payloads 20 that may be carried in the payload carrier 212 of various robots 210. The payload information database 270 may comprise information, for example, about exposure of various payloads 20 to various hazardous environments, including, e.g., tolerance for exposure to various levels of the hazardous gasses.

A hazardous environment detector (HED) 220A may be installed within the robotic system 200, e.g., on the robot 210, and/or an HED 220B may be placed at a location within the environment 10. The HED 220 may detect a variety of hazardous gasses as well as their concentration, and the airflow (direction, speed). There may be a plurality of HEDs 220 at various locations throughout the environment 10. Some gasses are heavier than air, and thus certain of the plurality of HEDs 220 may be located near the ground, whereas other gasses dissipate readily into the environment so that other HEDs 220 are located where such gasses may be present or predicted to move. The concentration of hazardous gasses at various locations, when combined with the airflow direction and speed, permits the HESC 250 to predict the flow of and concentration of the hazardous gasses at various positions and at various points in time. This determination may be made using, e.g., the Bernoulli principles associated with gas propagation. The speed/rate of hazardous gas leaking from the source may be determined and/or estimated based on data received from the various detectors 220.

In some embodiments, an artificial intelligence (AI) model may be utilized both to recognize the presence of various gas or other contaminants in the environment 10, as well as predict (using one or more prediction models), over time, the areas impacted by the gas/contaminants given other parameters described herein related to the environment 10. As such, a historical database may be kept of relevant information related to gas leaks, and this historical database may be utilized to create and evolve the AI model.

Boundaries for the environment 10 may be defined by building walls or other types of confinement barriers. However, boundaries for an environment 10 may also be defined where no physical barriers exist. In either case, the boundaries may be defined by using some form of a metes and bounds description, such as a geofence. Also, an environment 10 may be divided into sub-environments, and with further subdivisions, as needed.

The HESC 250 may further interface with a robot information database 260 and a payload information database 270 to determine which elements can exist in a particular hazardous environment. The robot information database 260 may contain information that specifies various tolerable concentration limits for various hazardous gasses for each robot 210, including those in operation and those awaiting operational orders. The robot information database 260 may further comprise information about the payload carrier 212 and the degree of protection the payload carrier 212 can provide to the payload 20 against various hazardous gasses. The degree of protection may be specified, e.g., as a reduction factor in terms of exposure. For example, a payload carrier 212 may specify a protection factor of 0.9, meaning that only 10% of a hazardous gas will penetrate the payload carrier 212 (or, put differently, the payload carrier 212 offers a 90% reduction in hazardous gas penetration). The protection factor may be time-based, meaning that the protection factor may vary over time. For example, for the first two minutes, the protection factor will be greater than 0.9, but will degrade to 0.8 by five minutes. The robot information database 260 may further comprise information about speed capabilities of the robot 210, which may be a factor used by the HESC 250 in calculating a time and trajectory to direct the robot to the safe location, e.g., what path the robot 210 should take to escape the hazardous environment.

Similarly, the payload information database 270 may contain information that specifies various tolerable concentration limits for various hazardous gasses for each payload 20 type. The concentration limits may also be time-based as well—meaning that x % of the payload may be compromised at a particular concentration after two minutes, and 2x % of the payload may be compromised at that particular concentration after five minutes. The payload information database 270 may apply the same types of information for the concentration limits, e.g., for a given amount of time, x % of the payload may be compromised, and for double the concentration of hazardous gas, 2x of the payload may be compromised in the same amount of time.

The robot information database 260 and the payload information database 270 may further comprise a temperature parameter as well, meaning that the temperature may impact how well the robot 210, its payload carrier 212, and the payload 20 itself respond to the hazardous gas. The curves for all of these variables (time, concentration, and temperature) as they relate to survivability may be linear or they may be representable by parametric curves. In some embodiments, temperature alone may constitute a hazardous environment, and thus survivability factors, as discussed herein, may be impacted solely by the temperature of the environment. As used herein, the term "hazardous gas" may also stand for, or be a proxy for, an environment that has no hazardous gas per se, but that constitutes a normal environment at a temperature that exceeds some upper and lower boundary range. The term "hazardous gas" may also be a proxy for other types of hazardous situations, such as an oil, acid, or other hazardous chemical leak, and the term "detectors" or "sensors" used herein may serve as a proxy for detectors of these additional types of hazardous situations.

Also, the survivability may be considered in terms of temporary or permanent damage. For example, a robot in a particular hazardous environment may only suffer temporary loss of function/capacity if it can be removed from the hazardous environment in a timely manner. However, in some hazardous environments, the robot may suffer permanent damage, or damage that requires express repair. Similarly, the survivability of the payload may be expressed in terms of an amount of the payload that survives. Tradeoffs may be made to favor one over the other. For example, pushing a robot 210 hard to escape a hazardous environment (e.g., escape in thirty seconds) may risk permanent damage to the robot 210, but minimal damage to the payload 20 (e.g., 5% damage), whereas pushing the robot 210 less hard (e.g., escape in two minutes) may only involve temporary damage, but create more damage to the payload (e.g., 20% damage).

The various detectors on the robot (220A) and within the environment (220B) detect the presence of a hazardous gas along with the airflow in the environment near the detector. The detectors 220 may have position-location components, such as global positioning system (GPS) detectors and/or location detection components that can determine a detector 220 location within a particular building or environment. In some embodiments, the location of, e.g., a detector 220B that is fixed in the environment may simply have its location assigned to it and this information may be stored within the HESC 250 or in some other location. Similarly, a detector 220A on the robot may not have its own position-sensing system but rather may make use of, and interface to, a position-determining system that may be a part of the robot 210 itself.

Figure 3:
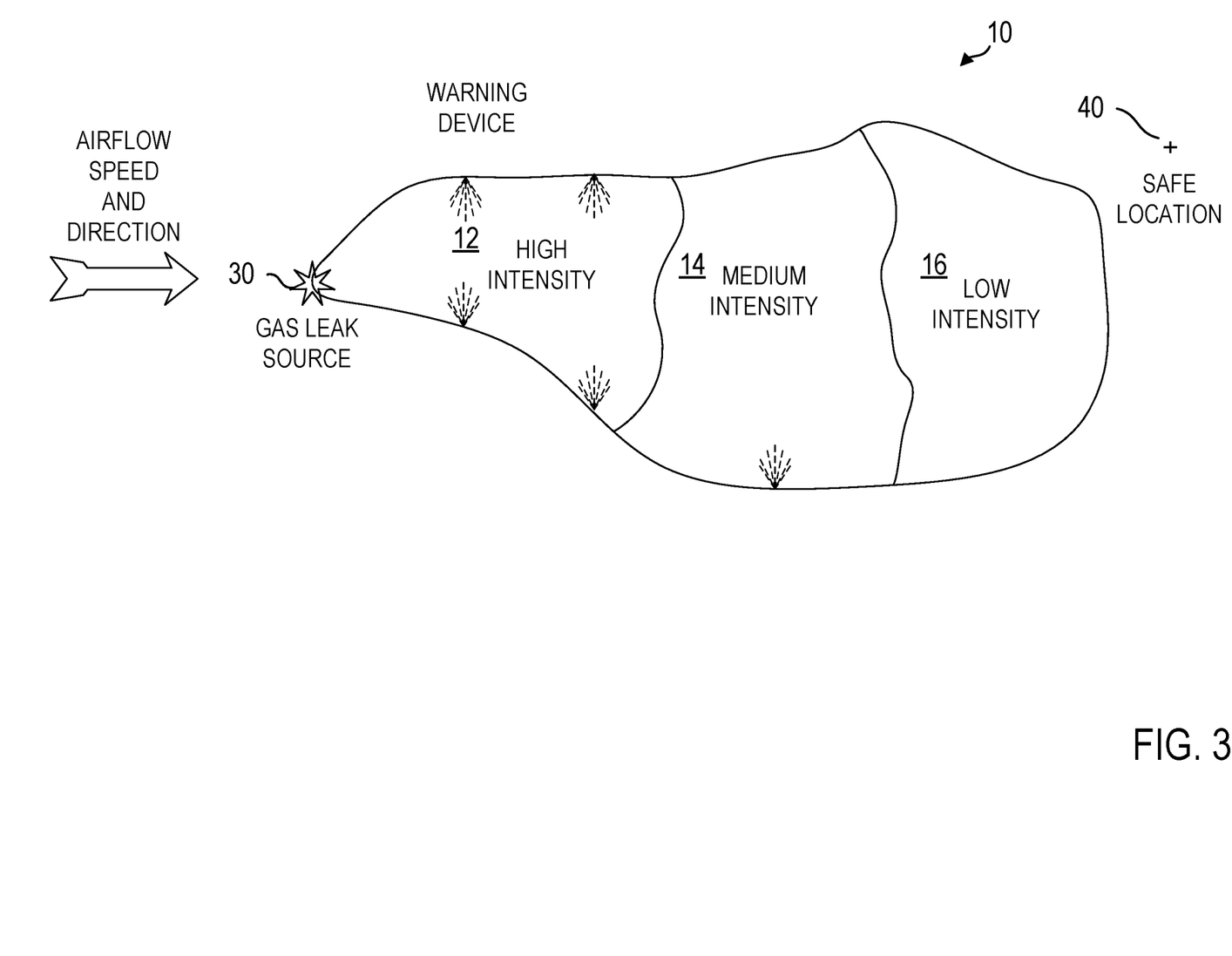
FIG. 3 is a pictorial diagram illustrating an operating environment for the robotic system, according to some embodiments.

With this information, a predicted spread of the hazardous gas may be determinable. Referring to FIG. 3, which is a pictorial diagram illustrating an example environment 10, at a specific point in time, a hazardous gas leak source 30 is present, and the gas is detected by a number of sensors 220 that may be located on the robot 210 and/or within the environment. The sensors 220 may also detect the airflow speed and direction at a particular location. This permits the HESC 250 to predict hazardous gas concentrations within a three-dimensional (3D) space over time.

As shown in FIG. 3, the HESC 250 has determined particular concentrations of the hazardous gas, and classified them (based, e.g., on predefined thresholds) into a high intensity region 12, a medium intensity region 14, and a low intensity region 16. These classifications or categorizations are arbitrary, and a greater number or fewer such categorizations may be implemented. These different categorized regions may be classified based on chances of an accident or damage to the robot 210 and/or the payload 20 it is carrying.

The concentrations, and hence, categorizations will change over time, based on the airflow speed and direction at each point-thus, a medium intensity region 14 may turn into a high intensity region 12 if the gas leak source 30 persists. Similarly, once the gas leak source 30 is under control, the high intensity region 12 may turn into a medium intensity region 14, and then a low intensity region 16 as the hazardous gas dissipates.

The HESC 250 may direct the robot 210 to escape a given region in the environment 10 if the gas concentration exceeds (or is predicted to exceed) a particular threshold established for the robot 210 and/or the payload 20. The escape need only be to a safe location 40 or within an area designated as safe for that robot 210 and/or the payload 20. Thus, the robot 210 may only need to be moved from the high intensity region 12 to the low intensity region 16 if the low intensity region has, or is predicted to have upon the robot's 210 arrival, an acceptable level of the hazardous gas. The timing of the movement may be based on any of the factors discussed above. Alternately, if the gas concentration for the robot is not predicted to be exceeded, but the gas concentration for the payload 20 is, the robot 210 may be instructed to activate additional protection that may be available for the payload carrier 212.

If the gas concentration exceeds (or is predicted to exceed) the threshold established for that particular robot 210, the HESC 250 may determine if another robot 210 is available that can tolerate the particular gas concentration. If this other robot 210 is available, it may be the substituted for the initial robot 210 that was determined to be unsuitable for the hazardous environment 10. In this situation, the robots that are not equipped to perform activity in the hazardous environment 10 may be] dynamically be repositioned in the area surrounding the hazardous environment 10 so that an appropriate movement path may be created for the robots 210 that are equipped to perform the activity in the hazardous environment 10. That is, the safe location 40 may be adjusted or maintained so that a movement path exists for the other robot to operate within the bounded environment 10. Once the problem is solved and the hazardous gas dissipates from the environment, as the hazardous gas concentration mitigates, the original robots 210 may be pressed back into service and resume their prior activities. In this way, hardened robots 210, which may be more expensive and/or have fewer capabilities, are only utilized when and where necessary, leaving the potentially less expensive robots 210 to perform their duties once there is no longer a hazardous environment.

If an attribute of the detected hazardous gas is that it is invisible, which will often be the case, then, in some embodiments, the HESC 250 may activate a warning device 230 to alert people nearby of the presence of the hazardous gas. In some embodiments, the warning device may be a terminal display that provides alert information to those nearby. In some embodiments, the HESC 250 may direct colored or clouded gas (non-hazardous) dispersal or dispensing devices 230 as a type of warning device 230 to mix colored fumes with the hazardous gas so that the propagation of the hazardous gas can be visualized.

The amount and/or intensity and/or type of the colored or clouded fume may, in some embodiments, be dispensed dependent on the concentration of the hazardous gas, types of hazardous gas, and the speed of propagation, so that based on the propagation of the hazardous gas can be visualized both by image sensors (not shown) on the robots 210 or by humans in the vicinity. In some embodiments, the propagation of the colored or clouded gas may be detected visually over time and compared with the prediction models in order to further enhance the prediction models' accuracy. The colored or clouded gas may be selected so that it has similar propagation characteristics to the detected hazardous gas. For example, if the hazardous gas is a heavy gas, a heavy colored or clouded gas that is also heavy may be selected.

In some embodiments where an attribute of the detected hazardous gas is that it is invisible and/or odorless, the warning device may direct the dispersal devices 230 to dispense a gas having a detectable odor (detectable by humans and/or detectors 220). This may be in place of or in addition to providing the colored or clouded gas, and may serve the same purpose as providing a warning as well as following the actual dispersal of the hazardous gas. The intensity of the odor may be proportional to the HGC.

Figure 4:
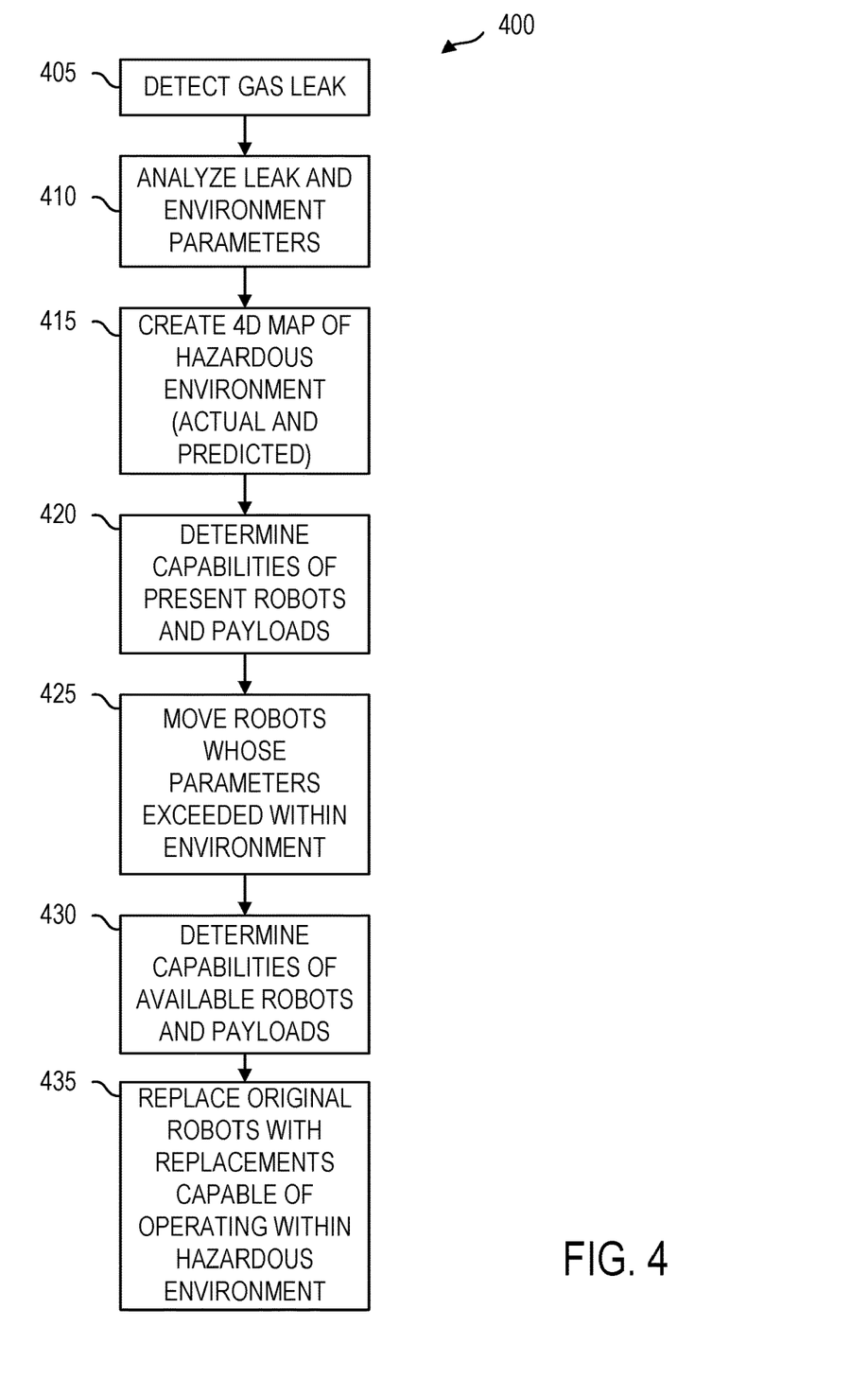
FIG. 4 is a flowchart illustrating an example embodiment of a process for operating the robotic system, according to some embodiments.

FIG. 4 is a flowchart illustrating an example process 400 according to some embodiments. In operation 405, the gas leak is detected by one or more of the detectors 220. In operation 410, the gas leak and environmental parameters, such as leak rate, wind speed, and wind direction, are obtained by the detectors 220, and values may be sent to the HESC 250 for analysis. In operation 415, a four-dimensional (4D) map of the hazardous environment is created (three spatial orthogonal dimensions actual and predicted across time)—this prediction may utilize the Bernoulli principles and, alternately or additionally, the AI component and/or historical information related to prior gas leaks in similar situations. In operation 420, the capabilities and tolerances of the present robots and their payloads is determined by the HECS 250. In operation 425, those robots 210 whose parameters (and/or payload parameters) are exceeded and that are located within the hazardous environment 10 are moved to the safe location 40. If other available robots have the capability of running in the hazardous environment (operation 430) (and they can adequately protect the payload 20 from the hazardous environment), then in operation 435, the original robots may be replaced with other robots capable of operating within the hazardous environment.

TECHNICAL APPLICATION

The one or more embodiments disclosed herein accordingly provide an improvement to technology, namely to improving the detection and avoidance by robots and/or their payload of a hazardous environment in which they might operate.

What is claimed is:

1. A computer-implemented method for protecting a robot in a hazardous environment, the method comprising:
    detecting, with a hazardous environment detector, a presence of a hazardous gas within a bounded environment defining boundaries of the hazardous environment, wherein an attribute of the hazardous gas is that the hazardous gas is invisible to a human eye;
    detecting a wind flow speed and wind flow direction proximate the hazardous environment detector;
    determining a hazardous gas concentration (HGC) that is at least one of a present HGC and a predicted future HGC;
    reading, from a database, a maximum HGC for at least one of the robot and a payload of the robot;
    conditioned upon the HGC exceeding a threshold value of the maximum HGC, directing the robot to move to a safe location in which the HGC does not exceed the threshold value of the maximum HGC; and
    dispensing, with a colored fume dispenser of a warning device, a colored or clouded fume, wherein the colored or the clouded fume intensity is dependent on a type of the hazardous gas.

2. The method of claim 1, further comprising:
creating a four-dimensional (4D) map, comprising three orthogonal spatial dimensions and one time dimension, of the environment that indicates or predicts the HGC at each point, wherein the creating of the 4D map uses a type of the hazardous gas, a rate of leaking of the hazardous gas, the wind flow speed, and the wind flow direction; and
using the 4D map, calculating a time and trajectory for a path of the robot to direct the robot to the safe location.

3. The method of claim 2, wherein the creating of the 4D map uses Bernoulli principles.

4. The method of claim 1, wherein the colored fume dispenser of the warning device is provided to alert people nearby of the presence of the hazardous gas.

5. The method of claim 1, further comprising:
determining that an attribute of the hazardous gas is odorless; and
directing the warning device, which comprises a gas having an odor fume dispensing device, to dispense a gas having an odor within the environment.

6. The method of claim 1, further comprising:
determining an availability of an other robot that is capable of safely operating within the bounded environment; and
adjusting or maintaining the safe location so that a movement path exists for the other robot to operate within the bounded environment.

7. The method of claim 1, wherein the HGC exceeds the threshold value only for the payload, the method further comprising:
determining an availability of an other robot that is capable of safely operating within the bounded environment and that the other robot comprises a payload carrier that protects the payload from the HGC.

8. The method of claim 1, further comprising:
conditioned upon the HGC no longer exceeding the threshold value of the maximum HGC, directing the robot to move from the safe location back to the bounded environment to resume normal operation.

9. A system for protecting a robot in a hazardous environment, the system comprising:
a memory; and
a processor that is configured to:
detect, with a hazardous environment detector, a presence of a hazardous gas within a bounded environment defining boundaries of the hazardous environment, wherein an attribute of the hazardous gas is that the hazardous gas is invisible to a human eye;
detect a wind flow speed and wind flow direction proximate the hazardous environment detector;
determine a hazardous gas concentration (HGC) that is at least one of a present HGC and a predicted future HGC;
read, from a database, a maximum HGC for at least one of the robot and a payload of the robot;
conditioned upon the HGC exceeding a threshold value of the maximum HGC, direct the robot to move to a safe location in which the HGC does not exceed the threshold value of the maximum HGC; and
dispense, with a colored fume dispenser of a warning device, a colored or clouded fume, wherein the colored or the clouded fume intensity is dependent on a type of the hazardous gas.

10. The system of claim 9, wherein the processor is further configured to:
create a four-dimensional (4D) map, comprising three orthogonal spatial dimensions and one time dimension, of the environment that indicates or predicts the HGC at each point using Bernoulli principles, wherein the creation of the 4D map uses a type of the hazardous gas, a rate of leaking of the hazardous gas, the wind flow speed, and the wind flow direction; and
use the 4D map, calculating a time and trajectory for a path of the robot to direct the robot to the safe location.

11. The system of claim 9, wherein the processor is further configured to:
determine that an attribute of the hazardous gas is odorless; and
direct a warning device, which comprises a fume dispenser for a gas having an odor fume and a colored fume, to release a gas having an odor and a gas that is colored or clouded within the environment.

12. The system of claim 9, wherein the processor is further configured to:
determine an availability of an other robot that is capable of safely operating within the bounded environment; and
adjust or maintain the safe location so that a movement path exists for the other robot to operate within the bounded environment.

13. The system of claim 9, wherein the HGC exceeds the threshold value only for the payload, processor being further configured to:
determine an availability of an other robot that is capable of safely operating within the bounded environment and that the other robot comprises a payload carrier that sufficiently protects the payload from the HGC.

14. The system of claim 9, wherein the processor is further configured to:
conditioned upon the HGC no longer exceeding the threshold value of the maximum HGC, direct the robot to move from the safe location back to the bounded environment to resume normal operation.

15. The system of claim 9, wherein the processor is further configured to:
create a four-dimensional (4D) map, comprising three orthogonal spatial dimensions and one time dimension, of the environment that indicates or predicts the HGC at each point using Bernoulli principles, wherein the creation of the 4D map uses a type of the hazardous gas, a rate of leaking of the hazardous gas, the wind flow speed, and the wind flow direction;
use the 4D map, calculating a time and trajectory for a path of the robot to direct the robot to the safe location;
determine that an attribute of the hazardous gas is at least one of invisibility and odorless;
direct a warning device, which comprises a gas having an odor fume and a colored fume dispenser, to release a gas having an odor and a gas that is colored or clouded within the environment;
determine the availability of an other robot that is capable of safely operating within the bounded environment;
adjust or maintain the safe location so that a movement path exists for the other robot to operate within the bounded environment;
determine the availability of an other robot that is capable of safely operating within the bounded environment and that the other robot comprises a payload carrier that sufficiently protects the payload from the HGC; and
conditioned upon the HGC no longer exceeding the threshold value of the maximum HGC, direct the robot to move from the safe location back to the bounded environment to resume normal operation.

16. A computer program product for an apparatus that protects a robot in a hazardous environment, the computer program product comprising:
one or more computer readable storage media, and program instructions collectively stored on the one or more computer readable storage media, the program instructions comprising program instructions to, when executed on a processor:
detect, with a hazardous environment detector, a presence of a hazardous gas within a bounded environment defining boundaries of the hazardous environment, wherein an attribute of the hazardous gas is that the hazardous gas is invisible to a human eye;
detect a wind flow speed and wind flow direction proximate the hazardous environment detector;
determine a hazardous gas concentration (HGC) that is at least one of a present HGC and a predicted future HGC;
read, from a database, a maximum HGC for at least one of the robot and a payload of the robot;
conditioned upon the HGC exceeding a threshold value of the maximum HGC, direct the robot to move to a safe location in which the HGC does not exceed the threshold value of the maximum HGC; and
dispense, with a colored fume dispenser of a warning device, a colored or clouded fume, wherein the colored or the clouded fume intensity is dependent on a type of the hazardous gas.

17. The computer program product of claim 16 wherein the program instructions further configure the processor to:
create a four-dimensional (4D) map, comprising three orthogonal spatial dimensions and one time dimension, of the environment that indicates or predicts the HGC at each point using Bernoulli principles, wherein the creation of the 4D map uses a type of the hazardous gas, a rate of leaking of the hazardous gas, the wind flow speed, and the wind flow direction;
use the 4D map, calculating a time and trajectory for a path of the robot to direct the robot to the safe location;
determine that an attribute of the hazardous gas is at least one of invisibility and odorless;
direct a warning device, which comprises a gas having an odor fume and a colored fume dispenser, to release a gas having an odor and a gas that is colored or clouded within the environment;
determine the availability of an other robot that is capable of safely operating within the bounded environment;
adjust or maintain the safe location so that a movement path exists for the other robot to operate within the bounded environment;
determine the availability of an other robot that is capable of safely operating within the bounded environment and that the other robot comprises a payload carrier that sufficiently protects the payload from the HGC; and
conditioned upon the HGC no longer exceeding the threshold value of the maximum HGC, direct the robot to move from the safe location back to the bounded environment to resume normal operation.

18. The computer program product of claim 16 wherein the program instructions further configure the processor to:
determine that an attribute of the hazardous gas is odorless; and
direct a warning device, which comprises a fume dispenser for a gas having an odor fume and a colored fume, to release a gas having an odor and a gas that is colored or clouded within the environment.

19. The computer program product of claim 16 wherein the program instructions further configure the processor to:
determine an availability of an other robot that is capable of safely operating within the bounded environment; and
adjust or maintain the safe location so that a movement path exists for the other robot to operate within the bounded environment.

\* \* \* \* \*